(12) United States Patent
Otto et al.

(10) Patent No.: US 8,551,704 B2
(45) Date of Patent: Oct. 8, 2013

(54) CONTROLLABLE STRAND SCISSION OF MINI CIRCLE DNA

(75) Inventors: Geoffrey Otto, San Carlos, CA (US); John Lyle, Redwood Shores, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 337 days.

(21) Appl. No.: 12/029,273

(22) Filed: Feb. 11, 2008

(65) Prior Publication Data

US 2008/0199874 A1 Aug. 21, 2008

Related U.S. Application Data

(60) Provisional application No. 60/890,392, filed on Feb. 16, 2007.

(51) Int. Cl.
C12Q 1/68 (2006.01)
C07H 21/04 (2006.01)

(52) U.S. Cl.
USPC ........................................ 435/6.12; 536/24.33

(58) Field of Classification Search
USPC .................................. 435/6, 91.2; 536/24.33
See application file for complete search history.

(56) References Cited

U.S. PATENT DOCUMENTS

| | | | |
|---|---|---|---|
| 5,001,050 A | 3/1991 | Blanco et al. | |
| 5,198,543 A | 3/1993 | Blanco et al. | |
| 5,268,267 A | 12/1993 | Smith | |
| 5,547,839 A | 8/1996 | Dower et al. | |
| 5,576,204 A | 11/1996 | Blanco et al. | |
| 5,648,245 A | 7/1997 | Fire et al. | |
| 5,714,320 A | 2/1998 | Kool | |
| 6,071,729 A | 6/2000 | Jeffries et al. | |
| 6,210,896 B1 | 4/2001 | Chan | |
| 6,255,083 B1 | 7/2001 | Williams | |
| 6,261,808 B1 | 7/2001 | Auerbach | |
| 6,312,913 B1 | 11/2001 | Wang et al. | |
| 6,498,023 B1 | 12/2002 | Abarzua | |
| 6,632,609 B2 | 10/2003 | Lizardi | |
| 6,787,308 B2 | 9/2004 | Balasubramanian et al. | |
| 6,828,100 B1 * | 12/2004 | Ronaghi | 435/6.12 |
| 7,056,661 B2 | 6/2006 | Korlach et al. | |
| 7,170,050 B2 | 1/2007 | Turner et al. | |
| 7,302,146 B2 * | 11/2007 | Turner et al. | 385/123 |
| 7,476,503 B2 | 1/2009 | Turner et al. | |
| 2002/0012933 A1 | 1/2002 | Rothberg et al. | |
| 2002/0168645 A1 | 11/2002 | Taylor | |
| 2003/0096253 A1 | 5/2003 | Nelson et al. | |
| 2003/0148988 A1 | 8/2003 | Kool | |
| 2003/0190647 A1 | 10/2003 | Odera | |
| 2003/0207267 A1 | 11/2003 | Lasken et al. | |
| 2003/0215862 A1 | 11/2003 | Parce et al. | |
| 2003/0235849 A1 | 12/2003 | Lizardi et al. | |
| 2004/0048300 A1 | 3/2004 | Sood et al. | |
| 2004/0152119 A1 | 8/2004 | Sood et al. | |
| 2004/0224319 A1 | 11/2004 | Sood et al. | |
| 2004/0259082 A1 | 12/2004 | Williams | |
| 2006/0024711 A1 | 2/2006 | Lapidus et al. | |
| 2007/0141598 A1 | 6/2007 | Turner | |
| 2008/0009007 A1 | 1/2008 | Lyle | |
| 2008/0233575 A1 | 9/2008 | Harris et al. | |
| 2009/0004666 A1 | 1/2009 | Tanabe et al. | |
| 2009/0305248 A1 | 12/2009 | Lander et al. | |

FOREIGN PATENT DOCUMENTS

| | | |
|---|---|---|
| WO | 91/06678 | 5/1991 |
| WO | 96/27025 | 9/1996 |
| WO | WO 9627025 A1 * | 9/1996 |
| WO | 99/05315 | 2/1999 |
| WO | 99/07896 A2 | 2/1999 |
| WO | 03/074734 A2 | 9/2003 |

OTHER PUBLICATIONS

Eid, et al. Science (2009) 323:133-138.
Fire et al., "Rolling replication of short DNA circles" PNAS (1995) 92:4641-4645.
Levene et al., "Zero-mode waveguides for single molecule analysis at high concentrations" Science (2003) 299:682-686.
Orrego et al., "Determination of familial relationships" PCR Protocols: A guide to methods and applications, eds. Innis et al., Academic Press Inc., San Diego, CA (1990) Ch. 50.
Tsukamoto et al., "A highly polymorphic CA repeat marker at the human tumor necrosis factor alfa locus" J Hum Gen (1998) 43:278-279.

* cited by examiner

*Primary Examiner* — Prabha Chunduru
(74) *Attorney, Agent, or Firm* — Deana A. Arnold

(57) ABSTRACT

The invention provides methods and compositions for the controlled termination of polymerase mediated primer extension reactions. The methods and compositions of the invention are broadly useful, and in a preferred aspect can be used in identifying sequence elements of template nucleic acids. Control of termination not only provides temporal control over termination, but, when used in conjunction with optically confined reaction regions, also spatially controls such termination.

18 Claims, 1 Drawing Sheet

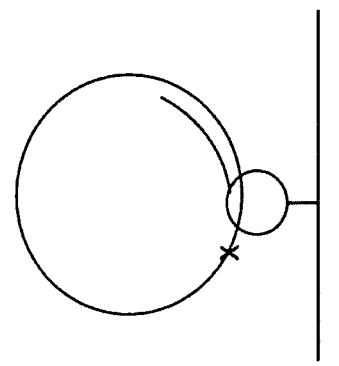
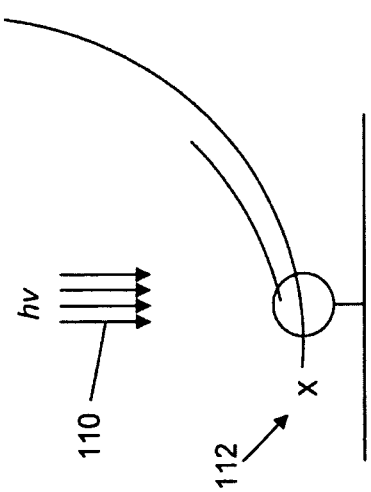
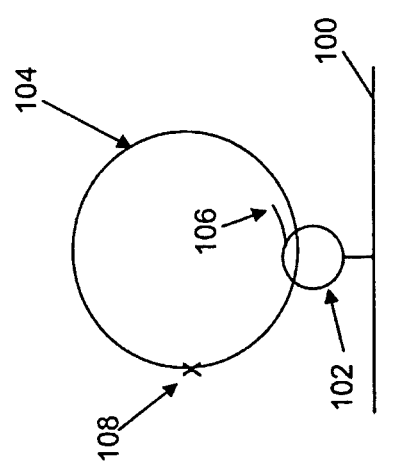

CONTROLLABLE STRAND SCISSION OF MINI CIRCLE DNA

CROSS-REFERENCE TO RELATED APPLICATIONS

This patent application claims the priority to Provisional U.S. Patent Application No. 60/890,392, filed Feb. 16, 2007, which is incorporated herein by reference in its entirety and for all purposes.

STATEMENT REGARDING FEDERALLY SPONSORED RESEARCH

Not applicable.

BACKGROUND OF THE INVENTION

In a large number of analytical reactions, the ability to precisely control reaction parameters is critical. This includes not only controlling basic parameters, such as pH, temperature and the chemical composition of the reactant, but also control over the initiation, termination, and the location of the reaction.

In nucleic acid analyses based on the detection of polymerase-mediated incorporation of nucleotides, control of the initiation of primer extension and the location of the reaction can be very useful, as set forth in copending U.S. Patent Application No. 60/814,433, filed Jun. 16, 2006 and incorporated herein by reference in its entirety for all purposes. Likewise, in many cases, e.g., where one desires to repeatedly perform extension reactions on multiple different primer or template combinations using the same enzyme system, the ability to terminate the interaction between the enzyme and the primer/template complex, thus making way for another primer/template complex, is also of substantial value. The present invention provides these and other benefits.

SUMMARY OF THE INVENTION

In particular, the present invention provides methods and compositions for controlling termination of polymerase mediated primer extension reactions, making the polymerase available for subsequent extension reactions with different primers and/or templates. Such methods may be broadly useful, but are particularly useful in identifying sequence elements of the template nucleic acid that rely upon the iterative primer extension on multiple template sequences. In accordance with the invention, the methods described herein not only provide temporal control over termination of primer extension reactions, but, when used in conjunction with optically confined reaction regions, also spatially controls such termination.

In a first aspect, the invention provides a method for the synthesis of a nucleic acid. The method comprises a complex which includes a polymerase, a first template, and a primer. The first template comprises at least one selectively cleavable linkage. The nucleic acid is synthesized by a polymerase mediated, first template dependent extension of the primer.

The invention also provides a composition that comprises a complex which includes a polymerase, a first template, and a primer. The first template in the compositions of the invention can include a selectively cleavable linkage.

In another aspect, the invention provides a device. The device comprises a complex disposed in a reaction region. The complex comprises a polymerase, a first template, a primer, and nucleoside triphosphates and/or analogues thereof. The first template comprises at least one selectively cleavable linkage.

The invention also provides a system which comprises a composition, a substrate and a cleavage agent.

In another aspect, the invention provides a method of identifying a base in a nucleic acid template. The method includes providing a complex which comprises a polymerase, a template and a primer. The template in turn comprises a cleavable linking group, which is cleaved to arrest synthesis. A base is identified in the nucleic acid template through the identification of one or more nucleotides or nucleotide analogues which are adjacent to the cleavable linking group in the template.

BRIEF DESCRIPTION OF THE DRAWINGS

FIG. 1 is a schematic illustration of the template dependent nucleic acid synthesis with controlled termination processes of the instant invention.

DETAILED DESCRIPTION OF THE INVENTION

The present invention is generally directed to activatable systems, methods and compositions for performing polymerase mediated, template dependent primer extension reactions. In particular, the invention provides methods for performing such reactions to determine sequence information for the template sequence using detection of nucleotides or nucleotide analogues incorporated onto the primer (or into the nascent strand).

The present invention provides a system for polymerase mediated, template dependent nucleic acid synthesis with controlled termination, and particularly nucleic acid synthesis with controlled termination that occurs substantially only within a desired analytical zone. By controlling the termination of the overall synthesis reaction, it is possible to prevent adverse effects of random termination, such as generation of reaction by-products that may interfere with the reaction or the monitoring of that reaction, generation of partially visible reaction components, and the like.

In a first aspect, the invention provides a method for synthesizing nucleic acids. The method comprises providing a complex which includes a polymerase enzyme, a first template, and a primer sequence. In accordance with the invention, the first template comprises at least one selectively cleavable linkage. When such a selectively cleavable linkage is cleaved, the result is a run-off point for the polymerase, which effectively frees the polymerase to bind a subsequent primer/template complex, allowing synthesis to continue with the subsequent primer/template complex. As a result, the overall synthesis reaction includes the ability to controllably terminate one particular template driven synthesis and exchange it for a new template driven synthesis. In a particularly preferred embodiment, once a desired level of primer extension is achieved on a given template, the cleavable linkage is cleaved, and the polymerase enzyme runs off the newly generated end of the template. A second primer template complex may then be bound by the polymerase enzyme and primer extension allowed to continue.

The general nature of the process is illustrated in FIG. 1. As shown, an immobilized DNA polymerase 102 is provided attached to a surface of a substrate 100. A first template sequence 104, shown as a circular template, is primed with an appropriate primer sequence 106, and allowed to interact with the polymerase 102 (Panel I), such that template directed, polymerase mediated DNA synthesis (also referred to as primer extension) occurs (see Panel II). In accordance with certain aspects of the invention, the template 104 includes a cleavable linkage 108 within its sequence. Upon exposure to an appropriate stimulus, e.g., a cleavage agent or electromagnetic radiation (shown by arrows 110 in Panel III), the cleavable linkage is severed, creating a new terminal point 112 for the template. Once the polymerase 102 in the primer extension reaction reaches the new terminal point 112 of the template, it will run off (Panel IV), and be available for primer extension using a subsequent primer/template complex.

In accordance with the present invention, the selectively cleavable linkage denotes a linkage in the particular polymeric strand of a nucleic acid polymer that may be cleaved upon exposure to an appropriate stimulus that may be selectively provided. Cleavage of the linkage will create a new 3' and 5' terminus. In the case of linear nucleic acids, this will result in two separate strands, each having its own 3' and 5' termini, while circular nucleic acids will be linearized. Cleavable linkages may include linking groups that are selectively cleavable by exposure to chemical agents, e.g., acid or base labile groups, specifically targeted nucleases or restriction enzymes, or the like, or they may include linking groups that are cleavable by exposure to external electromagnetic energy, e.g., UV or other light, heat or combinations thereof. In particularly preferred aspects, the selectively cleavable groups are not cleaved under conventional polymerase mediated DNA synthesis conditions, e.g., temperature, pH, present reagents. In still more preferred aspects, the conditions under which cleavage occurs will not substantially damage or negatively impact the activity of the polymerase enzyme.

In a particularly preferred aspect, the selectively cleavable linkage may include a specific site or sub-sequence of nucleotides incorporated into the template sequence, which may be cleaved by exposure to the appropriate enzyme or other agent such as a restriction endonuclease. As will be appreciated, in order to provide optimal control over synthesis termination, it will be preferred that only a single restriction or cleavage site be present in a given template, so as to avoid termination in undesired portions of the template. As such, and in the case of restriction sites, it may be desirable to use particularly rare restriction sequences or include restriction sequences that are known not to be otherwise present in the template. Thus, in accordance with a preferred embodiment of the invention, an exogenous restriction site is incorporated into the template to be used as a selectively cleavable linkage, as distinguished from the exploitation of restriction sites already present in the template. Examples of restriction sites that can be utilized in accordance with the invention include, without limitation: AatII, Acc65I, AccI, AciI, AclI, AcuI, AfeI, AflII, AflIII, AgeI, AhdI, AleI, AluI, AlwI, AlwNI, ApaI, ApaLI, ApeKI, ApoI, AscI, AseI, AsiSI, AvaI, AvaII, AvrII, BaeI, BamHI, BanI, BanII, BbsI, BbvCI, BbvI, BccI, BceAI, BcgI, BciVI, BclI, BfaI, BftiAI, BglI, BglII, BlpI, Bme1580I, BmgBI, BmrI, BmtI, BpmI, Bpu10I, BpuEI, BsaAI, BsaBI, BsaHI, BsaI, BsaJI, BsaWI, BsaXI, BseRI, BseYI, BsgI, BsiEI, BsiHKAI, BsiWI, BslI, BsmAI, BsmBI, BsmFI, BsmI, BsoBI, Bsp1286I, BspCNI, BspDI, BspEI, BspHI, BspMI, BspQI, BsrBI, BsrDI, BsrFI, BsrGI, BsrI, BssHII, BssKI, BssSI, BstAPI, BstBI, BstEII, BstNI, BstUI, BstXI, BstYI, BstZ17I, Bsu36I, BtgI, BtgZI, BtsCI, BtsI, Cac8I, ClaI, CspCI, CviAII, CviKI-1, CviQI, DdeI, DpnI, DpnII, DraI, DraIII, DrdI, EaeI, EagI, EarI, EciI, EcoNI, EcoO109I, EcoP15I, EcoRI, EcoRV, FatI, FauI, Fnu4HI, FokI, FseI, FspI, HaeII, HaeIII, HgaI, HhaI, HincII, HindIII, HinfI, HinPII, HpaI, HpaII, HphI, Hpy188I, Hpy188III, Hpy99I, HpyCH4III, HpyCH4IV, HpyCH4V, KasI, KpnI, MboI, MboII, MfeI, MluI, MlyI, MmeI, MnlI, MscI, MseI, MslI, MspA1I, MspI, MwoI, NaeI, NarI, NciI, NcoI, NdeI, NgoMIV, NheI, NlaIII, NlaIV, NotI, NruI, NsiI, NspI, PacI, PaeR7I, PciI, PflFI, PflMI, PhoI, PleI, PmeI, PmlI, PpuMI, PshAI, PsiI, PspGI, PspOMI, PspXI, PstI, PvuI, PvuII, RsaI, RsrII, SacI, SacII, SalI, SapI, Sau3AI, Sau96I, SbfI, ScaI, ScrFI, SexAI, SfaNI, SfcI, SfiI, SfoI, SgrAI, SmaI, SmlI, SnaBI, SpeI, SphI, SspI, StuI, StyD4I, StyI, SwaI, Taq$^\alpha$I, TfiI, TliI, TseI, Tsp45I, Tsp509I, TspMI, TspRI, Tth111I, XbaI, XcmI, XhoI, XmaI, XmnI, and ZraI.

In certain aspects, the selectively cleavable linkage may include a photocleavable linkage joining adjacent nucleotides within the template. Such a linkage may be selectively cleaved upon exposure to light of an appropriate wavelength. A variety of photocleavable linking chemistries are known in the art and include, e.g., p-nitrobenzyloxymethyl ether, p-methoxybenzylether, p-nitrobenzylether, mono-, di- and tri-methoxytrityls, 7-nitroindole 2'-deoxyribonucleoside (see e.g., Crey-Desbiolles et al., *Nucleic Acids Research*, (2005), Vol. 33(5):1532-43, fully incorporated herein by reference in its entirety for all purposes), diphenylmethylsilyl ether, sisyl ether, 3',5'-dimethoxybenzoincarbonate, 1-(4,5-dimethoxy-2-nitro-phenyl)ethyl ester, 2-(2-nitrophenyl)ethoxycarbonyl, [(α-methyl-2-nitropiperonyl)-oxy]carbonyl, methanesulfate, tosylate, non-nucleosidic aminotag phosphoramidites (see e.g., Olejnik et al., *Nucleic Acids Research*, (1998), Vol. 26(15): 3572-76 and Albert et al., *Nucleic Acids Research*, (2003), Vol. 31(7):e35, both fully incorporated herein by reference in its entirety for all purposes), 1-pyrenylmethyloxycarbonyl, anthracenylmethyloxycarbonyl, rhodium complexes including Rh(phi) complexes, cobalt complexes including Co(III)-bleomycin, anthraquinone derivatives, naphthalimides, anthryl derivatives, benzotriazole derivatives, quinolines and quinoxalines, naphthyridines and fluoroquinolones, diazo derivatives, arylazides, arylhydrazines and diphenyl arylhydrazidophosphates, amitryptiline and imipramine, porphyrins, and the like. These and a variety of other photocleavable linkages may be employed in conjunction with this aspect of the invention, as described in, e.g., the *CRC Handbook of Organic Photochemistry and Photobiology* (Second Edition, 2003), and *Protective Groups in Organic Synthesis* (T. W. Greene and P. G. Wuts, 3rd Ed., John Wiley & Sons, 1999), each of which is incorporated herein by reference in its entirety for all purposes. As will be appreciated, in the case where one wishes primer extension to continue over the cleavable linkage, e.g., in the case of a circular template, cleavable linkages that are used will be compatible with polymerase/template interaction for primer extension.

In alternative aspects, the selectively cleavable linkage may include linking groups between adjacent nucleotides in the template that may be selectively cleaved through exposure to elevated temperatures.

In a preferred aspect of the invention, a nucleic acid is synthesized by a polymerase mediated first template dependent extension of the primer. In certain particularly preferred embodiments, the selectively cleavable linkage does not include a restriction site. Such a selectively cleavable linkage may be cleaved upon exposure to light, heat, and temperature as described herein.

The methods of the invention are particularly useful in performing nucleic acid sequence analyses, and more particularly "sequence-by-incorporation" reactions where the sequence of bases in a nucleic acid sequence are identified based upon the template dependent incorporation of complementary nucleotides by polymerase enzyme.

A variety of sequence-by-incorporation techniques have generally been described. For example, in certain methods, a DNA polymerase complexed with a template sequence and an appropriate primer is exposed to an individual type of nucleotide base. The complex is then examined to determine whether the particular base was incorporated into the extended primer sequence by the polymerase. Identification of incorporation is carried out by either looking for an incorporated label in the extended primer sequence or by assaying the reaction mixture for pyrophosphate which would be released upon incorporation of a base (i.e., "pyrosequencing"). The complex is iteratively and separately exposed to each of the chemical groups that prevent any additional bases from being added to the extending primer, thus allowing incorporation of one and only one base in any given round. These sequencing methods are generally discussed in U.S. Pat. Nos. 6,833,246, 6,210,891, and 6,258,568, the full disclosures of each of which are hereby incorporated herein by reference in their entirety for all purposes.

In a preferred aspect, the methods of the invention are employed in a single molecule, real-time sequence by incorporation process, e.g., as described in U.S. Pat. Nos. 6,753,200, 7,033,764, 7,056,661, and 7,056,676 and Levene et al., Science 299:682-686, January 2003 *Zero-Mode Waveguides for Single-Molecule Analysis at High Concentration*, the full disclosures of each of which are hereby incorporated herein by reference in their entirety for all purposes. Briefly, a polymerase/template/primer complex is provided immobilized upon a surface of a substrate, and the complex is exposed to a complete set of four nucleotides or nucleotide analogs. The analogs are labeled such that incorporation of each nucleotide into the extending primer releases the label from the nucleotide. Preferred nucleotide and nucleotide analogs are described in e.g., the above-incorporated patents, and U.S. Pat. Nos. 7,041,812 and 7,052,839, the full disclosures of which are incorporated herein by reference in their entirety for all purposes.

In order to observe the individual complexes at reagent concentrations that are more biologically relevant, the complexes may be provided on the surfaces such that they are individually spatially resolvable, and/or within an optically confined illumination volume, such that the complex is illuminated without illuminating much of the surrounding reaction mixture.

Optically confined analysis regions may be achieved in a variety of ways. For example, by using total internal reflectance microscopy, one can provide a very thin layer of illumination on an opposing side of a transparent substrate. Stated briefly, directing light at a transparent substrate at an angle that results in total internal reflection of the light beam will still yield some propagation of light beyond the substrate that decays exponentially over a very short distance, e.g., on the order of nanometers. By illuminating a reaction mixture on a substrate using total internal reflection through the substrate, one can effectively confine illumination to a very thin layer of the reaction mixture adjacent to the substrate, thereby providing an optically confined reaction region or volume.

Examples of particularly preferred confined illumination techniques include zero mode waveguides, as described in detail in U.S. Pat. Nos. 6,991,726 and 7,013,054, each of which is incorporated herein by reference in its entirety for all purposes. In such aspects, the polymerase/template/primer complex is provided immobilized within the illumination volume of the zero-mode waveguide. Briefly described, a zero mode waveguide typically includes a transparent substrate that has an opaque cladding layer deposited upon its surface. The cladding layer may be a variety of different types of opaque materials, including semiconductors, opaque polymers, metal films, and the like. In particularly preferred aspects, metal films and more preferably, aluminum of chrome films are used as the cladding layer.

By providing for an optically activatable system, one can further enhance the application of the system by selecting for active complexes that fall within the optically accessible portion of the analytical system. Rephrased, by only activating complexes that fall within an illumination region of a substrate, one ensures that only those complexes within the illuminated region are active, and thus reduce any interference from active complexes that are outside the illuminated region. Similar concepts have been described for immobilization within optically confined regions by optically activating coupling groups only within the optically confined region, e.g., within an illumination volume of a zero mode waveguide (See, e.g., commonly assigned U.S. patent application Ser. No. 11/394,352, filed Mar. 30, 2006, which is incorporated herein by reference in its entirety for all purposes).

In the context of sequence by incorporation methods, the methods of the present invention provide a controllable process for releasing a template sequence from the polymerase complex, thus effectively terminating or arresting the sequencing reaction with respect to the template. In particular, by selectively cleaving the template sequence, the polymerase enzyme will run out of template and the template will be released. As a result, the polymerase is available for complexing with a subsequent template, i.e., a second template, in order to continue the sequencing analysis.

Although primarily illustrated and of primary value for use with circular template sequences, e.g., as shown in FIG. 1, it will be appreciated that the usefulness of the present invention is not restricted to circular templates, but may also be of value in linear templates where one wishes to have the ability to selectively abbreviate the sequencing reaction with respect to a given template, e.g., through cleavage of an intermediate base linkage. As a result, the templates of the present invention may include a variety of general structures, including, e.g., circular and linear templates. Similarly, although generally described in terms of DNA templates, it will be appreciated that for different applications these templates may comprise DNA, RNA, and non-naturally occurring nucleic acids.

As noted above, the methods of the present invention often include a step of bringing a second or subsequent template into contact with the polymerase in an iterative process. As with the first template, in preferred aspects, the second template may include a cleavable linkage as set forth herein. As will be appreciated, where chemical or enzymatic cleavage is carried out, it may be necessary to remove any residual cleavage agent from the reaction mixture prior to introducing the subsequent template, e.g., through an appropriate washing step that removes the agent without removing the polymerase. In certain aspects, however, each subsequent template sequence may include a different cleavable linkage, e.g., a different restriction site, such that cleavage agents for the first template will not act upon the second or other subsequent template. As a result, the need for any washing step may be substantially obviated.

Introduction of cleavage agents into the reaction mixture may be accomplished by a variety of methods. For example, cleavage agents, subsequent templates, or any other added reagents may be injected into a given reaction mixture using standard fluid handling robotic systems, e.g., robotic pipettors such as the Twister® systems available from Caliper Life Sciences, Inc. (Hopkinton, Mass.). Alternative methods of reagent introduction may rely upon microfluidic manifolds integrated over reaction arrays, e.g., multiwell plates, for introducing precise amounts of reagents into each of a number of reaction wells. In addition to the above described methods, the invention also provides compositions, substrates and devices that are used in carrying out those methods. For example, the invention provides a nucleic acid polymerization complex that includes a polymerase enzyme, a template sequence that includes a cleavable linkage as described herein, and optionally, a primer sequence. The polymerases of the invention may include any polymerase enzyme suitable for a given application, including, e.g., DNA polymerase I and modified DNA polymerase I (e.g., Klenow Fragment), Taq polymerase, T3 polymerase, T4 polymerase, T7 polymerase, Bst polymerase, 9° $N_m$™ polymerase, reverse transcriptase, terminal deoxynucleotidyl transferase, poly A polymerase, SP6 polymerase, RB69 polymerase, pol α polymerase, pol β polymerase, Eco pol I polymerase, and the like. In a preferred embodiment, the polymerases of the invention include Phi29 polymerase and modified Phi29-like DNA polymerases, e.g., as described in copending U.S. patent application Ser. Nos. 11/645,125, 11/645,135, 11/645,223, each filed Dec. 21, 2006, and incorporated herein by reference in their entirety for all purposes.

The present invention also encompasses devices that include the compositions of the invention. For example, in preferred aspects, the aforementioned complexes will be disposed within a reaction region of a reaction vessel in order to carry out the desired reaction. In some cases, the reaction region may comprise a reaction well in a multiwell plate or a surface region of a substrate, with or without additional structural confinements for the reaction mixture. In particularly preferred aspects, the complex is provided immobilized upon a surface of a substrate, and as such, the reaction region will include that surface region of the substrate. Such substrates, again, may include surfaces of wells in multiwell plates or otherwise, as described above.

In certain aspects, the complex is immobilized upon a transparent substrate such that the primer extension reaction may be monitored as it progresses. Such transparent substrates will typically include silica based substrates, e.g., fused silica, quartz, borosilicate glass, etc., and polymeric substrates, e.g., PMMA, polystyrene, polypropylene, etc. In further preferred aspects, the substrates will comprise glass substrate layers having optical confinements disposed thereon, e.g., zero mode waveguides as described herein, where the complexes are provided immobilized within the core regions of the zero mode waveguides.

What is claimed is:

1. A method for the synthesis of a nucleic acid comprising:
providing a complex, wherein said complex comprises a polymerase, a first template, nucleoside triphosphates and/or analogues thereof, and a primer, wherein said first template comprises at least one selectively cleavable linkage within a nucleotide sequence of the template, and further wherein said first template is a circular template;
cleaving said selectively cleavable linkage to provide a new terminus in the template in the complex; and
synthesizing said nucleic acid by polymerase mediated, first template dependent extension of said primer.

2. The method of claim 1, wherein said cleaving said selectively cleavable linkage arrests said synthesis of said nucleic acid.

3. The method of claim 1, wherein subsequent to said cleaving of said cleavable linkage, said first template is replaced by a second template, and synthesizing said nucleic acid is resumed by a polymerase mediated, second template dependent extension of said primer.

4. The method of claim 1, wherein said cleavable linkage is selected from the group consisting of a photocleavable linkage and an enzymatically cleavable linkage.

5. The method of claim 1, wherein said selectively cleavable linkage comprises a restriction site.

6. The method of claim 1, wherein said complex is immobilized upon a surface of a substrate.

7. The method of claim 6, wherein said at least one of said polymerase, first template, nucleoside triphosphates and/or analogues thereof, and primer of said complex is immobilized upon said surface of said substrate.

8. The method of claim 7, wherein said polymerase is immobilized upon said surface of said substrate.

9. The method of claim 7, wherein said first template is immobilized upon said surface of said substrate, 10. The method of claim 7, wherein said nucleoside triphosphates and/or analogues thereof are immobilized upon said surface of said substrate.

11. The method of claim 7, wherein said printer is immobilized upon said surface of said substrate.

12. The method of claim 6, wherein said complex is immobilized in an optically confined region on said surface of said substrate.

13. The method of claim 6, wherein said substrate is transparent.

14. The method of claim 12, wherein said complex is immobilized within art illumination volume of a zero mode waveguide.

15. A method of identifying a base in a nucleic acid template, comprising:
providing a polymerase/template/primer complex, wherein the template comprises a cleavable linking group within a nucleotide sequence of the template, and further wherein said template is a circular template;
cleaving the cleavable linking group to arrest synthesis;
identifying one or more nucleotides or nucleotide analogues adjacent to said cleavable linking group, thereby identifying a base in said nucleic acid template.

16. The method of claim 15, wherein said cleavable linking group is selected from the group consisting of a photocleavable linking group and an enzymatically cleavable linking group.

17. The method of claim 1, wherein said new terminus is a new 5' terminus.

18. The method of claim 17, wherein said new 5' terminus is a run-off point for the polymerase.

* * * * *

UNITED STATES PATENT AND TRADEMARK OFFICE
CERTIFICATE OF CORRECTION

| | | |
|---|---|---|
| PATENT NO. | : 8,551,704 B2 | Page 1 of 1 |
| APPLICATION NO. | : 12/029273 | |
| DATED | : October 8, 2013 | |
| INVENTOR(S) | : Geoffrey Otto and John Lyle | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 411 days.

Signed and Sealed this
Twenty-fourth Day of February, 2015

Michelle K. Lee
*Deputy Director of the United States Patent and Trademark Office*